United States Patent [19]

Zickel

[11] 4,011,863
[45] Mar. 15, 1977

[54] SUPRACONDYLAR PROSTHETIC NAIL

[76] Inventor: Robert E. Zickel, 235 E. 42nd St., New York, N.Y. 10017

[22] Filed: July 19, 1976

[21] Appl. No.: 706,470

[52] U.S. Cl. .................. 128/92 BA; 128/92 BC
[51] Int. Cl.$^2$ .................. A61F 5/04; A61B 17/18
[58] Field of Search .......... 128/92 R, 92 B, 92 BA, 128/92 BC, 83

[56] References Cited

UNITED STATES PATENTS

| | | | |
|---|---|---|---|
| 2,579,968 | 12/1951 | Rush | 128/92 BC |
| 2,998,007 | 8/1961 | Herzog | 128/92 BC |
| 3,433,220 | 3/1969 | Zickel | 128/92 BC |
| 3,439,671 | 4/1969 | Kuntscher | 128/92 R |

FOREIGN PATENTS OR APPLICATIONS

| | | | |
|---|---|---|---|
| 2,341,439 | 2/1975 | Germany | 128/92 BC |

OTHER PUBLICATIONS

"Internal Fixation For Supracondylar Fracture Of The Femur in The Elderly Patient" by A. Brown et al. The Journal of Bone and Joint Surgery, British vol. 53-B, No. 3, Aug., 1971, pp. 420–424.
Zimmer Advertisement p. 5, The Journal of Bone and Joint Surgery, vol. 37A, July, 1955.
Lock the Bone with Dynamics; Oblique Fractures – Short Fragments, The Rush Medullary Pin, Advertisement pp. 42–43, The Journal of Bone and Joint Surgery, Sept., 1960.

*Primary Examiner*—Ronald L. Frinks
*Attorney, Agent, or Firm*—Connolly and Hutz

[57] ABSTRACT

A prosthetic nail for stabilizing fractures in the supracondylar area of the femur has an elongated flat shape and tapers substantially over its entire length from a relatively thick head (about 0.4 × 0.5 inch) to a relatively thin tip (about 0.2 × 0.05 inch). The elevational configuration of the nail has a thin elongated midportion (about 0.1 inch thick) with two curved ends. The larger head end is about 0.5 inch thick formed by inside and outside radii about 2 and 3 inches long. The curved head end extends longitudinally about 2.5 inches from the midportion. The thinner tip end has a radius of about 1.75 inches extending longitudinally about 1 inch. The plan configuration of the nail is about 11 inches long tapering from a 0.4 inch wide head to about a 0.2 inch blunt rounded tip. A hole for a lag screw is provided through the head end either at right angles to the elevational length of the nail or at a slight inward inclination thereto. The lag screw is threaded for retention in bone and varies in length from about 2 to 3 inches.

10 Claims, 8 Drawing Figures

U.S. Patent — Mar. 15, 1977 — 4,011,863
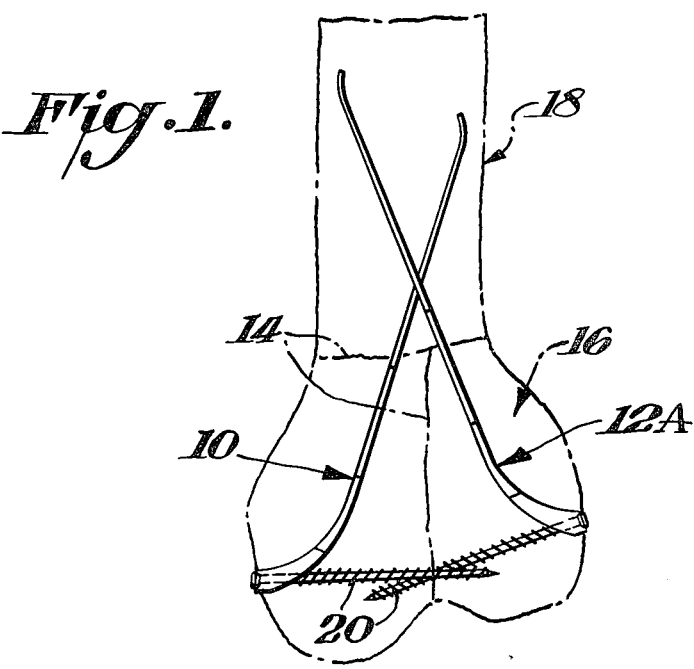
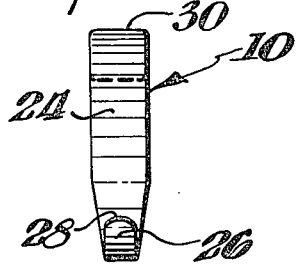
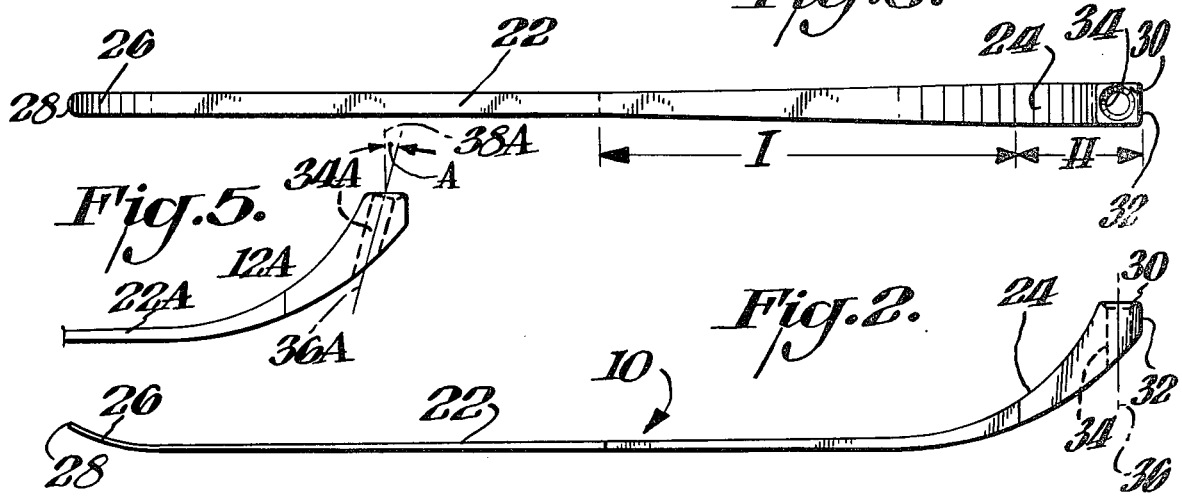

SUPRACONDYLAR PROSTHETIC NAIL

BACKGROUND OF THE INVENTION

Various elongated nails of biocompatible metal are used for stabilizing fractures in bones. Such nails usually have a pointed tip end and a larger head secured to the bone in which they are implanted. An object of this invention is to provide an efficient prosthetic nail for stabilizing fractures in the supracondylar area of the femur.

SUMMARY

In accordance with this invention a prosthetic nail is made flat with substantially rectangular cross sections tapering from a larger (0.4 × 0.5 inch) head to a thin (0.2 × 0.05 inch) blunt rounded tip. The plan configuration of the nail tapers from a 0.4 inch head to a 0.2 inch flat blunt. The elevational configuration has a relatively thin tapered midsection about 0.1 inch thick with two upwardly curved ends. The head end arcuately tapers out to a 0.5 inch thick head, which retains a lag screw for a length of about 2.5 inches. The tip has a radius of about 1.75 inches for a length of about 1 inch. The head is squared off about the lag screw hole which is disposed at a suitable angle for insertion in the bone such as perpendicular to the length of the nail or at a slightly smaller angle. The lag screw has threads and a length suitable for retention in the bone, for example, from about 2 to 3 inches.

BRIEF DESCRIPTION OF THE DRAWINGS

Novel features and advantages of the present invention will become apparent to one skilled in the art from a reading of the following detailed description in conjunction with the accompanying drawings wherein similar reference characters refer to similar parts and in which:

FIG. 1 is a schematic view in elevation of a fractured supracondylar portion of the femur with a pair of prosthetic nails of this invention inserted therein;

FIG. 2 is a view in elevation of one of the supracondylar prosthetic nails shown in FIG. 1;

FIG. 3 is a top plan view of the nail shown in FIG. 2;

FIG. 4 is a left end view in elevation of the nail shown in FIG. 2;

FIG. 5 is a partial view of a modification of the nail shown in FIG. 2;

FIG. 6 is a view in elevation of one of the lag screws shown in FIG. 1;

FIG. 7 is a left end head view of the lag screw shown in FIG. 6; and

FIG. 8 is a right end tip view of the lag screw shown in FIG. 6.

DESCRIPTION OF THE PREFERRED EMBODIMENTS

In FIG. 1 is shown a pair of supracondylar prosthetic nails 10 and 12A securing a T-shaped fracture designated by phantom lines 14 in the supracondylar area 16 of femur 18, which is partially shown in FIG. 1. Lag screw 20 secures the head of nails 10 and 12A to the supracondylar area of femur 18 and secure the split condylar portions of femur 18 together. Nails 10 and 12 are inserted with their longer ends disposed within the intramedullary canal (not shown) of femur 18.

FIGS. 2–4 show details of nail 10. An elevational configuration is shown in FIG. 2 with a substantially straight thin midportion 22 disposed between upwardly curved head end 24 and upwardly curved tip end 26. Midportion 22 tapers from a maximum thickness of about 0.5 inch (3.43 mm) to a minimum thickness of about 0.055 inch (1.40). Head end 24 is formed for example by an outer radius of 3.25 inches (82.5 mm) having a center of rotation disposed 3.115 inches (75.12 mm) above midportion 22. The inner radius of 2.25 inches (57.1 mm) is tangent to the upper edge of midportion 22. Curved head portion extends about 2.5 inches (63.5 mm) longitudinally from straight midportion 22. Curved tip end 26 extends longitudinally about 1 inch from straight midportion 22, has parallel outer and upper radii of about 1.75 inch (44.4 mm) forming an arc of about 30°.

FIG. 3 shows the plan configuration with a tapered intermediate portion I extending from about 4.25 inches (107.9 mm) from a distance H about 1.25 inside (31.7 mm) from the head of nail 10. Intermediate portion I tapers from about 0.410 inch (10.41 mm) adjacent the head of nail 10 to 0.224 inch (5.63 mm). The rest of the plan configuration of nail 10 has parallel sides. Plan tip 28 has a rounded blunt end of full radius.

Head end 24 shown in FIG. 2 has square top and side ends, 30 and 32, which contain hole 34 for receiving lag screw 20 shown in FIGS. 6–8. Hole 34 has its axis 36 disposed substantially perpendicular to the length of nail 10. This is described as a lateral configuration for lag screw 20. FIG. 5 shows what is described as a medial disposition for lag screw 20 by inclination of its axis 36A inwardly at an angle A of about 15° relative to a perpendicular line 38A to the length of nail 12A. Lag screw holes 34 and 34A have upper counter-sunk ends 40 and 40A.

Supracondylar nails 10 and 12A may be used for stabilizing various types of fractures of the supracondylar area of the femur either singly or in pairs. Nails 10 and 12A and screws 20 are made of a biocompatible metal such as Vitallium. Vitallium is the trademark of Howmedica, Inc., for a special cobalt-chromium alloy developed and used for cast partial and full dentures and for internal applications by surgeons. Cobalt and chromium constitute over 90% of its composition. Vitallium is characterized by a specific gravity of 8.29; tensile strength, 95,000 lb./sq. in. minimum; 2% offset yield strength, 65,000 lb/sq.in.minimum; reduction of area, 8% minimum, elongation 8% minimum; and modulus of elasticity, 30,000,000–32,000,000 lb./sq.in. When polished it is exceedingly smooth and permanently lustrous. Its outstanding qualities are clinical inertness in relation to living tissues and high degree of resistance to corrosion.

The flat configuration of nails 10 and 12A helps prevent rotational displacement of the implanted nail. The gently taper over substantially the entire length of the nails provides variable resistance to bending in different portions of its length in a manner similar to that obtained by a varying layer spring. The blunt dull tip end prevents the wall of the intramedullary canal from being pierced. Nails 10 and 12A are intended for use in stabilizing fractures in the distal one-third area of the femur, for repairing various types of fractures such as T-shaped, condylar or any other fracture in the distal one-third area.

FIGS. 6–8 show lag screw 20 which may vary in length, for example from about 2 to 3 inches. It has a tapered flat head with a hexagonal socket. The tip is pointed and has V-shaped self-tapping threads for firm bone engagement.

I claim:

1. A supracondylar prosthetic nail comprising a substantially flat elongated length of biocompatible metal having plan and elevational configurations, the plan configuration tapering from a relatively larger head to a rounded blunt tip about half the thickness of the head, the elevational configuration having a relatively thin tapered elongated midportion and arcuate head and tip ends extending on the same side of the midportion, the arcuate head end having ample inner and outer radii providing a thickness at the extremity similar to that of the plan head configuration, the arcuate tip end of the elevational configuration having relatively smaller radii smoothly continuing the smaller end of the midportion a short distance, and a hole for a retaining screw through the end of the head being disposed substantially at right angles to the midportion in the elevational configuration.

2. A supracondylar prosthetic nail as set forth in claim 1 wherein the retaining screw hole has an axis, and the axis is disposed at right angles to the midportion of the nail in elevational configuration.

3. A supracondylar prosthetic nail as set forth in claim 1 wherein the retaining screw hole has an axis, and the axis is disposed at slightly less than right angles to the midportion of the nail in elevational configuration.

4. A supracondylar prosthetic nail as set forth in claim 1 wherein the plan configuration has a tapered intermediate portion and substantially parallel sided head and tip sections connected thereto, and the tapered intermediate portion has a ratio of taper of about two to one from wider to narrower ends.

5. A supracondylar prosthetic nail as set forth in claim 1 wherein the midportion in elevational configuration tapers from a thickness of about 0.1 to 0.5 inch, the arcuate head end tapers outwardly to a thickness of about 0.5 inch, and the arcuate tip end substantially continues the thickness of the thinner portion of the midportion.

6. A supracondylar prosthetic nail as set forth in claim 5 wherein the terminal end of the head on plan configuration is about 0.4 inch wide.

7. A supracondylar prosthetic nail as set forth in claim 6 wherein the nail is about 11 inches long.

8. A supracondylar prosthetic nail as set forth in claim 1 wherein the arcuate head and tip ends are substantially about 2.5 and 1.0 inch long.

9. A supracondylar prosthetic nail as set forth in claim 8 wherein the intermediate portion is between about 4 or 5 inches long.

10. A supracondylar prosthetic nail as set forth in claim 1 wherein the head end in elevational configuration is squared off at its top and terminal sides about the lag screw hole.

* * * * *